United States Patent [19]
Galli

[11] Patent Number: 5,546,932
[45] Date of Patent: Aug. 20, 1996

[54] POWDER JET DISPENSER FOR MEDICAMENT INHALATION THERAPIES

[75] Inventor: Rosaria Galli, Camogli, Italy

[73] Assignee: Tebro SA, Luxemborg, Luxembourg

[21] Appl. No.: 313,033

[22] PCT Filed: Mar. 24, 1993

[86] PCT No.: PCT/IT93/00024

§ 371 Date: Nov. 15, 1994

§ 102(e) Date: Nov. 15, 1994

[87] PCT Pub. No.: WO93/18812

PCT Pub. Date: Sep. 30, 1993

[30] Foreign Application Priority Data

Mar. 25, 1992 [IT] Italy ............................. GE92A0030
Dec. 23, 1992 [IT] Italy ............................. GE92A0134

[51] Int. Cl.$^6$ ......................................... A61M 15/00
[52] U.S. Cl. ............................. 128/203.15; 128/203.23
[58] Field of Search ................... 128/200.14, 200.22, 128/202.21, 203.15, 203.19, 203.21, 203.23

[56] References Cited

U.S. PATENT DOCUMENTS 3,921,637 11/1975 Bennie et al. .
4,524,769 6/1985 Wetterlin .............................. 128/203.15

FOREIGN PATENT DOCUMENTS

2238505 2/1975 France .
2282279 3/1976 France .
2926659 1/1981 Germany .......................... 128/203.15
8806288 9/1988 Germany .
2144997 3/1985 United Kingdom .
2165159 4/1986 United Kingdom .............. 128/203.15
9114468 10/1991 WIPO .
92/02268 2/1992 WIPO .............................. 128/203.15
9204068 3/1992 WIPO .
9220455 11/1992 WIPO .

*Primary Examiner*—Ren Yan
*Assistant Examiner*—Eric P. Raciti
*Attorney, Agent, or Firm*—Sughrue, Mion, Zinn, Macpeak & Seas

[57] ABSTRACT

A powder jet dispenser for medicament inhalation therapies, intended to be the drug pack container, incorporating a dose metering system, comprising a filling unit (27, 28, 29, 30, 31, 35) and a separation unit (25, 26) to fill a fix positioned dosage chamber (19) and to provide, after filling, air-tight separation of the filling unit from the medicament reservoir (36). The dosage chamber (19) being connected to a compression chamber (5) of a servo-assisted air compression system actuated by a manual stroke of a plunger (3) providing the compression of a spiral load spring (7). The load spring is released through a sliding control mechanism (11, 14) which is automatically actuated by the stroke of the plunger (3). The load spring (7) bears against a piston (8) which, upon release, snaps forward into said compression chamber (5) producing a jet of compressed air which reaches the dosage chamber (19), and passes the drug into the user's mouth through a nozzle (20) provided with a check valve (22) to avoid the entrance of external air.

21 Claims, 9 Drawing Sheets

POWDER JET DISPENSER FOR MEDICAMENT INHALATION THERAPIES

BACKGROUND OF THE INVENTION

In the pharmaceutical field several lung diseases, like bronchial asthma, are treated with powdered drugs to be delivered, by means of dispensing inhalation devices, in very accurate doses to be frequently repeated.

A dispensing device for these drugs should guarantee an accurate and reproducible dosage, a perfect nebulization, which means the reduction of the powder to "respirable particles" having a diameter of less than 7 microns, avoiding or disintegrating eventual powder lumps, and the powderized drug isolation from the outside environment, to ensure its stability and preservation.

These three characteristics, dosage accuracy, fineness of nebulization and drug stability have, up to now, been obtained all together only with the use of aerosol metered dispensers provided with a container in which the powderized drug is dispersed into pressurized FREON.

But the aerosol system and its relative FREON or CFC propellent shall not be further allowed in the near future and furthermore the use of propeleny in general requires to add to the drug tensioactive or lubricant additives which have shown negative side effects when inhaled.

A way of administering powderizod drug able to avoid the use of CFC propellent and additives is represented by the powder inhaler devices.

The main characteristic of these devices is that the delivery of the drug is obtained by the air flow generated at inhalation which, passing through a dosage chamber containing the powderized drug, forms the particle cloud which is then inhaled, thus avoiding the need of propellent.

In these systems, as the powderized drug, particles often tend to lump together forming too large particles to be inhaled, the user has to provide an inhalation flow whose force is enough high to first move the particles and then disintegrate them during their run through the inhaler conduits.

This breathing force cannot be achieved by many asthmatic patient and therefore only very low dosage devices and drugs have demonstrated to be enough widely usable in most of the situations.

The document WO-A-9 204 068 discloses an inhalator without propellant gas comprising a triggerable pump which can be manually precharged before starting inhalation and can be triggered in synchronism with the respiration. Disadvantageously, this device is very complicated and may therefore lead to failures and problems during the operation and the assembly process. Furthermore, in operation, the dosage chamber is moved from the reservoir in an air channel, whereby some of the content of the dosage chamber can be lost before the air stream blows through the air channel. The dosage accuracy is therefore not guaranteed.

To overcome this problem, some inhalers use packs capsules each containing a single dose of the powderized drug, and more recently systems incorporating a multidose powder reservoir have been introduced on the market.

One of the most recent version of this system incorporates one or more dosage chambers, obtained as holes in a rotable element associated to the drug reservoir, holes which are filled by dosage means contained into the drug reservoir.

These means consist in elastic spring loaded scrapers arranged to press against the perforated element surface.

These scrapers, due to their flexed position at an angle lower than 90° degrees against the perforated element and thanks to the thrust given by the spring loading and by their resilient characteristics, do exert a pressure on the micronized powder and compress it into, the dosage holes when they slide under them.

Nevertheless this compression of the powderized drug could create, in certain cases, some inconvenient which could compromise the dose accuracy.

In fact the micronized powders, when compressed, tend to stick together and to form lumps of various and relatively large dimension, and scrapers in general, keep under compression at least the quantity of drug which is retained between themselves and the rigid surface against which they urge.

These agglomerates are not always removed or disintegrated by the scrapers and could therefore obstacle the correct filling of the dosage holes or chambers.

Further to that this compression could create "compactings" of different and not controllable density inside the dosage holes, thus creating possible variations in the delivered quantities.

The above is further particularly relevant in case of relatively large required doses (from 2 to 10 mg and over) as in the use of Sodium Cromoglycate or of mixtures of different drugs.

In these cases, in fact, larger and mainly deeper dosage holes are needed, which makes their filling much more difficult.

Furthermore the deeper holes reduce the effectiveness of a scraper as a filling device as, due to its shape, it cannot enter deep into the hole to be filled.

SUMMARY OF THE INVENTION

The object of the present invention is to provide a system allowing to replace the pressurized aerosol propellent system and its relative additives, with pressurized air whose pressure is generated, at the moment of the administration, by a suitable device, which is part of the medicament pack, which also incorporates a dosage system able to provide dosage accuracy and reproducibility together with medicament stability and preservation.

A further object is to provide the possibility of a coordination between the inhalation and the actuation of the device in order to allow the medicament to effectively reach the lungs of the patient.

The present invention relates to a powder jet dispenser for medicament inhalation using environment air, compressed at the moment of the dispenser actuation, ejected, at predetermined and reproducible quantity, pressure and speed, from a compression chamber by means of a manually spring loaded and servo-assisted piston, ejection performed through a passage connecting the compression chamber to the dosage one which is further connected to the dispenser nozzle.

Dosage chamber which is accurately and reproducibly filled by filling means contained inside the powderized medicament reservoir and that, further to the chamber filling, provide for the isolation of the medicament reservoir from the outside environment, and the compressed air flow.

The above with the further advantage to allow to replace the manual control of the release of the spring loaded piston and the consequent- drug delivery with a control system directly and automatically actuated by the air flow generated at inhalation.

It is thus provided a powder jet dispenser serving as medicament pack container for medicament inhalation therapies comprising a dose metering system having filling means and a separation unit to fill a dosage chamber arranged at the bottom of a medicament reservoir and to provide, after its filling, the air-tight separation from the medicament reservoir, said dosage chamber being connected to a compression cylindrical chamber formed in a tubular element which is part of an air compression system actuated by the stroke of a plunger and accumulating energy by means of the compression of a spiral load spring, and then automatically releasing said accumulated energy of said spiral load spring by means of a sliding control mechanism automatically actuated either by the continuation of the stroke of the plunger, or in a modified embodiment, by an element directly controlled by the user's inhalation, said accumulated energy being released against a piston which under the thrust of the load spring snaps forwardly into said compression chamber, thereby producing a jet of compressed air for the medicament delivery from the dosage chamber through a nozzle, characterized in that said filling means are rotatable and said dosage chamber is fixed, said dosage chamber being formed in the bottom of said medicament reservoir.

In accordance with these constructional features, it is possible to refill the dosage chamber by simply turning the filling means, which is a very simple operation for the user and provides high reliability in supplying only a limited amount of product. Furthermore, it is impossible to lose a part of the dosage chamber content before the air stream blows through it. A high dosage accuracy and reproducibility is thereby provided. It is further provided a jet dispenser for medicareant inhalation, therapies manually actuated by means of a cylindrical plunger axially slidable inside a hollow main body, plunger which contains, inside its cavity, a piston subjected to the thrust of a cylindrical main load spring and is slidable assembled inside a hollow cylinder forming the compression chamber for the air, and having an axial outlet hole provided with a non return valve, said cylinder having axially and externally slidable mounted a control sleeve, provided with a secondary return spring, suitable to force a resilient expansible detent ring, operating in a slotted groove formed on the hollow cylinder, to inwardly protrude and oppose the forward movement of the piston during all the manual loading and compression of the main spring by means of the pressure exerted on the plunger; plunger which at the end of its loading stroke abuts with its edge against the edge of said control sleeve and shifts it forward thus allowing the resilient expansible detent ring to expand and therefore to release the piston which, under the action of the loaded spring, moves forward with a strong snap action and produces a jet of compressed air at high speed and pressure which are predetermined by the elastic characteristics of the spring and by the dimensions of the compression chamber, both to be chosen in relation to the quantity and the type of drug to be delivered.

Said compressed air reaches, through a suitable passage, a dosage chamber containing the exact quantity of powderized drug to be delivered, powder which has been previously inserted by means of the filling and separating device contained into the drug reservoir, and gets out, in form of a mixed jet, through a nozzle provided with a separation non return valve.

Said filling and separating device consisting in elements, connected to a turning knot, placed outside the powder dispenser, carrying two or more brushes, or better little brooms, preferably of different length and softness, able to penetrate and fill the dosage chamber obtained as a hole made on the bottom of the drug reservoir, and a plug, which separates the dosage chamber and the compressed air flow from the drug reservoir, once the turning knob is returned to a marked position after the turn made to obtain the filling of the dosage chamber.

The above with the further possibility to obtain a breath control of the actuation (by inhalation) of the dispenser instead of a manual one, by associating with the control sleeve a lever element provided with two side arms carrying the lever rotation fulcrum consisting in two pins, passing through two diametrically opposite special slits made on the control sleeve, and inserted into two blind holes made on the hollow cylinder, forming the compression chamber. Said lever element provided, associated with each of the fulcrum pins, with a cam, interacting with the suitably shaped slit profile of the control sleeve, and having its terminal part, opposite to said two side arms, shaped in the form of a semicylindrical vane which is inserted into a special control chamber, formed into the external body of the dispenser, provided with slits for the air inlet which are normally closed by the same vane, and connected, by means of suitable passages, made inside the dispenser body, to the dispenser mouthpiece.

The above suitably arranged so that the vane, at the inhalation made by the patient, and the consequent depression created into the control chamber, moves to let the air in causing the rotation of the lever, of which it is part, on its fulcrum pins.

Rotation which, thanks to the cams, provided on the side arms of the lever, acting against the profile of the slits made into the control sleeve, causes the shift of the latter and the consequent release of the resilient expansible detent ring and of the piston which snaps forward, instantly releasing the energy accumulated while manually, loading the ma-in spring and causing a compressed air jet at high and predetermined speed and pressure.

BRIEF DESCRIPTION OF THE DRAWINGS

The accompanying drawings show in different scales, by way of non limiting examples, a basic embodiment of the article of the invention and a simplified and modified version, incorporating the breath control actuation.

DETAILED DESCRIPTION OF THE PREFERRED EMBODIMENTS

Figure 1:
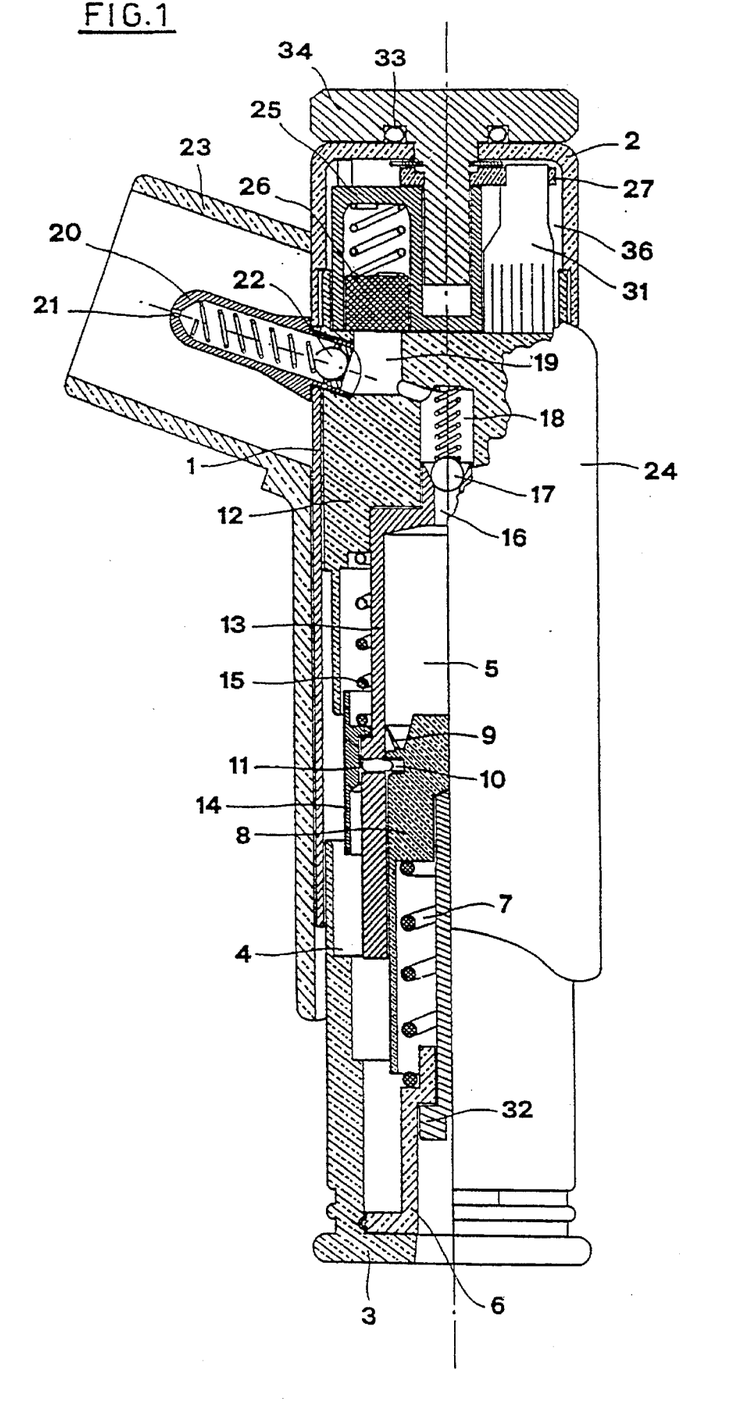
FIG. 1.—Is an axial sectional view of the powder dispenser being concerned, with its internal components parts, the drug reservoir and the nozzle, in a basic embodiment and at the rest position with the plunger ready to start the stroke to load the main spring.

As clearly shown in FIG. 1, the powder jet dispenser for medicament oral inhalation being concerned, which is at the same time the medicament pack, consists in a tubular main body 1 bearing, screwed or in other way fixed on its upper end, the cover 2, of the powderizod drug reservoir, which support the filling system and on the opposite side axially sliding a cylindrical cup shaped actuation plunger 3 provided with shoulder 4 on its bore and bearing a cylindrical base 6, fastened to its bottom, intended to support and guide a cylindrical load main spring 7 mounted inside a partly hollow piston 8 with blind head provided with a seal lip 9 and with a circular grove 10 intended to house, during the spring 7 loading action, part of the resilient expansible detent ring 11.

Said piston 8 to which is connected the screw 32 which interacts with the cylindrical base 6 and the cylindrical actuation plunger 3 during the manual resetting of the system later on described.

Figure 2:
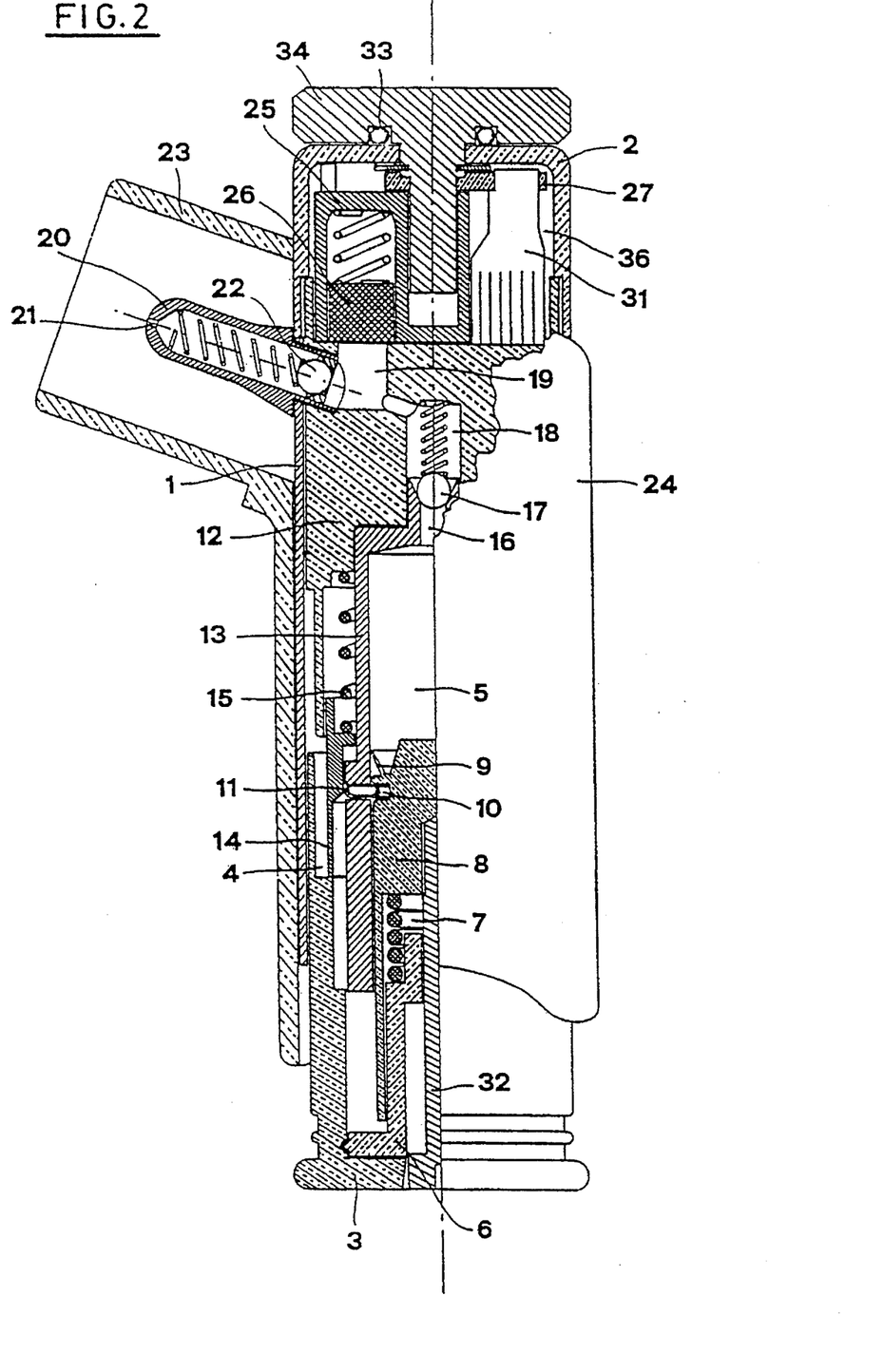
FIG. 2.—Is an axial sectional view similar to FIG. 1 with the spring loading stroke almost completed and immediately before the piston snaps and the consequent air compression occurs.

Under the drug reservoir the tubular main body retains a separation and distribution head provided with a protruding cup shaped neck and with a seat to fix and retain a tubular element 13, protruding towards the cylindrical plunger 3, and intended to form the air compression chamber 5 inside which the piston 8 slides, and retain in a special slotted groove the resilient expansible detent ring 11 which tends to outwardly protrude but is forced, in the phases shown in FIGS. 1 and 2, to protrude inwardly of the tubular element 13 and to enter the circular groove 10 made on the head of the pistor, 8, thus opposing the forward movement of the same piston 8.

This position and locking function of the elastic expansible detent ring 11 is granted by the sliding control sleeve 14 pushed towards the shoulder 4 of the cylindrical plunger by the secondary return spring 15.

The control sleeve 14 is internally shaped in such a way that it can act as a cam for the resilient expansible detent ring 11 and to keep it compressed during all the loading action of the main spring 7 obtained by pressing the cylindrical plunger 3.

At the end of the main spring loading phase, as shown in FIG. 2, the shoulder 4 of the cylindrical plunge 3 abuts against the lower edge of the control sleeve 14.

The further movement of the cylindrical plunger 3 causes the control sleeve 14 to shift and, thanks to its internal cam profile, to permits the resilient expansible detent ring to expand.

Figure 3:
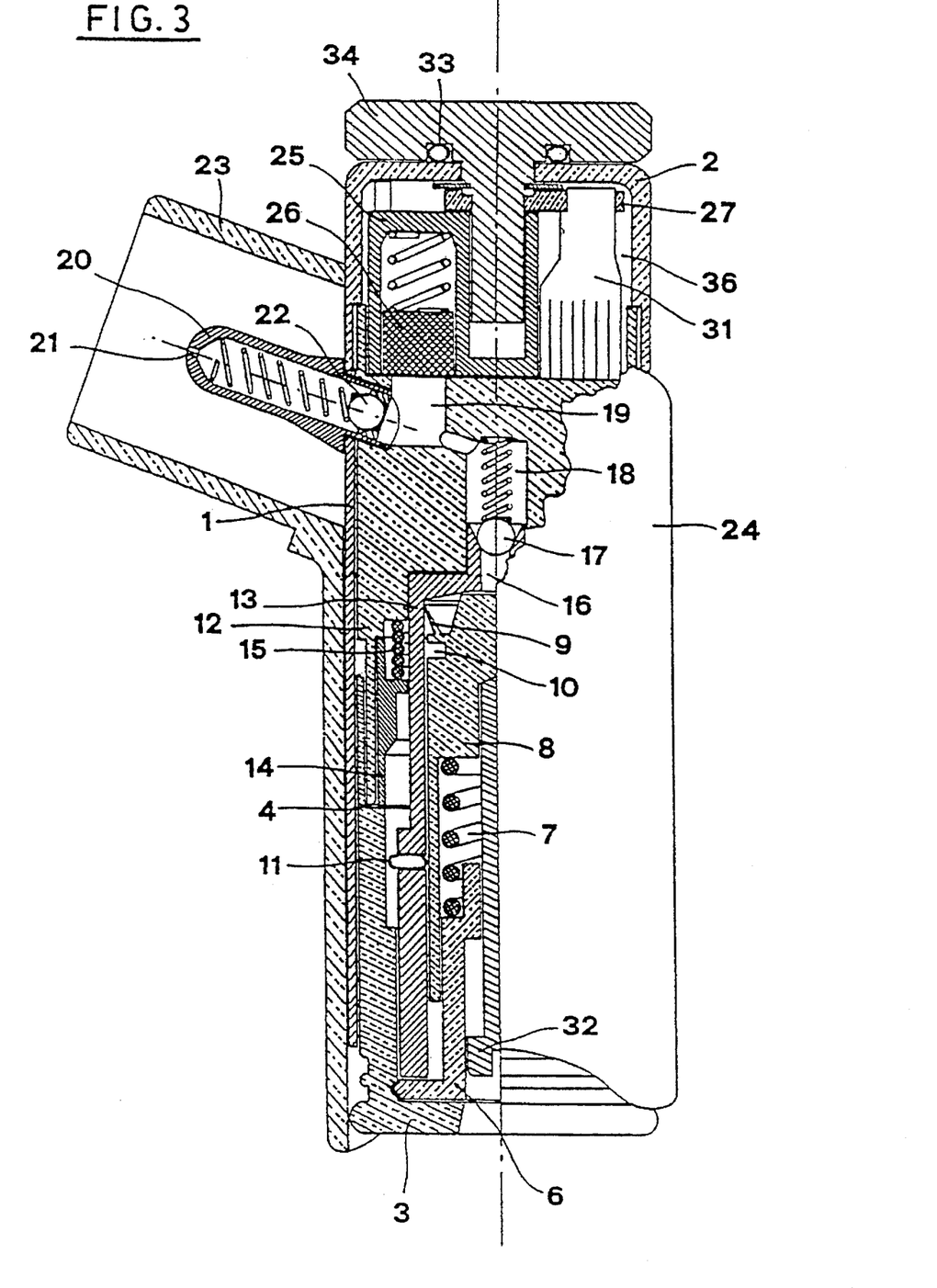
FIG. 3.—Is an axial sectional view similar to FIGS. 1 and 2 with the dispenser at the end of the delivery.

As result its inward protruding portion retracts from the circular groove 10 on the head of the piston 8, and the piston, due to the action of the loaded spring 7, moves forward with a strong snap action, reaching the position of FIG. 3, and causes the compression of the air volume contained in the compression chamber 5 and its expulsion through the central passage 16, of the tubular element 13, provided at its outlet with a sphere check valve 17; passage 16 which is connected to a chamber 18, formed inside the head 12, containing a little load spring for the check valve 17.

The chamber 18 is connected, by a lateral passage, to the dosage chamber 19, containing the exact dose of powderized drug to be delivered, which is further connected to the drug reservoir from which it is filled by the filling device, better described later on, which, being provided with the plug 26, also grant the closure and the separation of the same dosage chamber from the drug reservoir chamber 36. This separation avoid any compressed air dispersion or drug return into the drug reservoir, during the compressed air flow and the consequent drug delivery, thus granting that all the drug contained into the dosage chamber 19 is effectively delivered and exploiting all the compressed air force available.

The dosage chamber 19 which is fixed with respect to the main body 1, is also provided with an outlet passage connected to the nozzle 20 provided with a calibrated passage 21 and containing a sphere check valve 22 having the function to prevent, after the drug delivery, the entrance of outside air.

In order to facilitate the use of the dispenser the nozzle 20 is surrounded by a short coaxial hose or mouthpiece 23 formed in the external casing 24 of the main body 1 of the dispenser.

Figure 8:
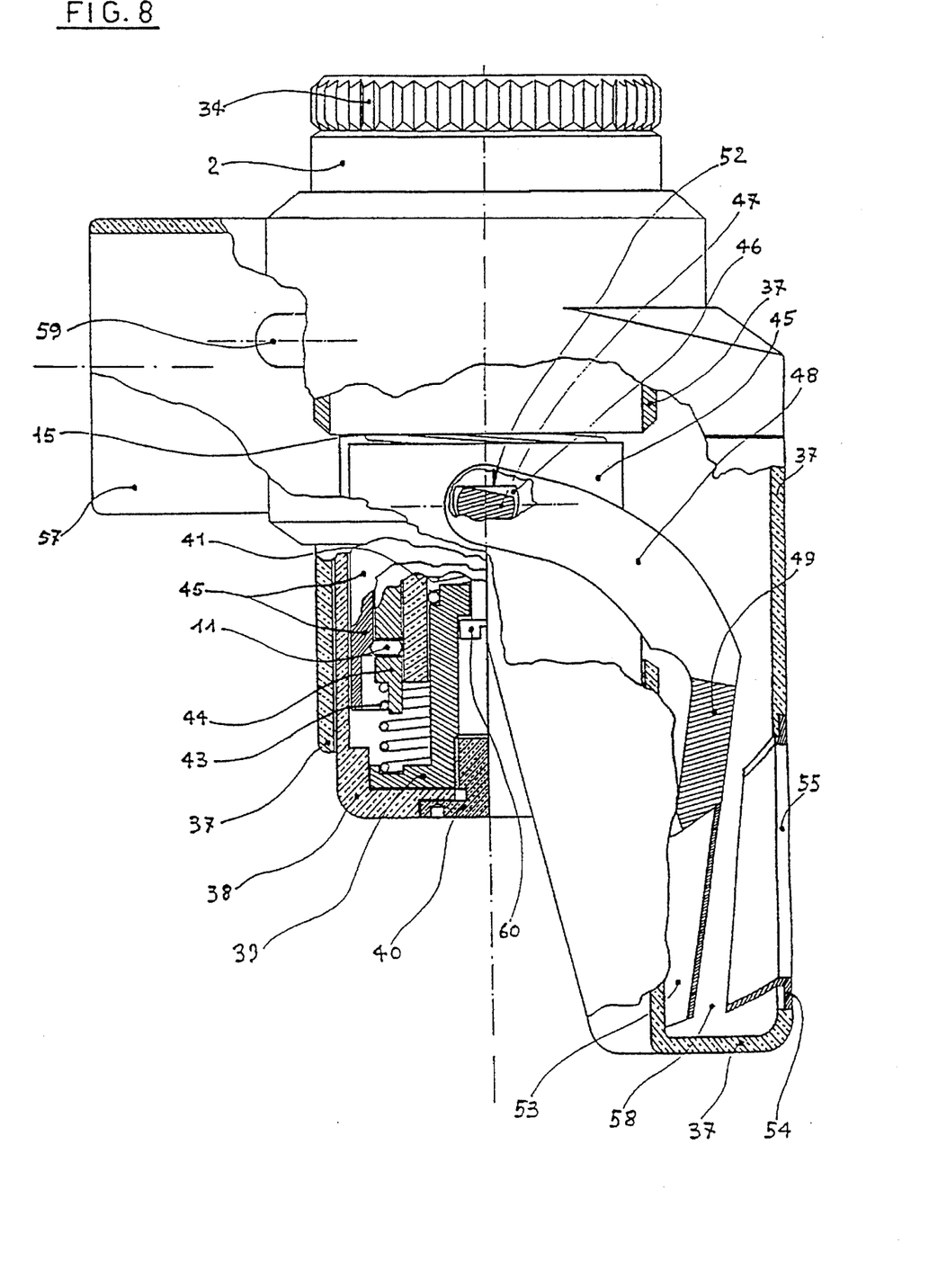
FIG. 8.—Is an axial partly sectional view similar to FIG. 7 but with the dispenser during the drug delivery.

At the end of the drug delivery and in the position described in FIG. 8, after a first phase of automatic return, due to the thrust of the secondary spring 15 against the control sleeve 14 which acts against the shoulder 4 of the plunger 3, the unit is returned to the position described in FIG. 1 by exerting a manual pull action on the cylindrical plunger 3.

This action also reset the piston 8, thanks to the head of the screw 32 acting against an inner shoulder of the cylindrical base 8 fixed to the cylindrical plunger 3.

Figure 4:
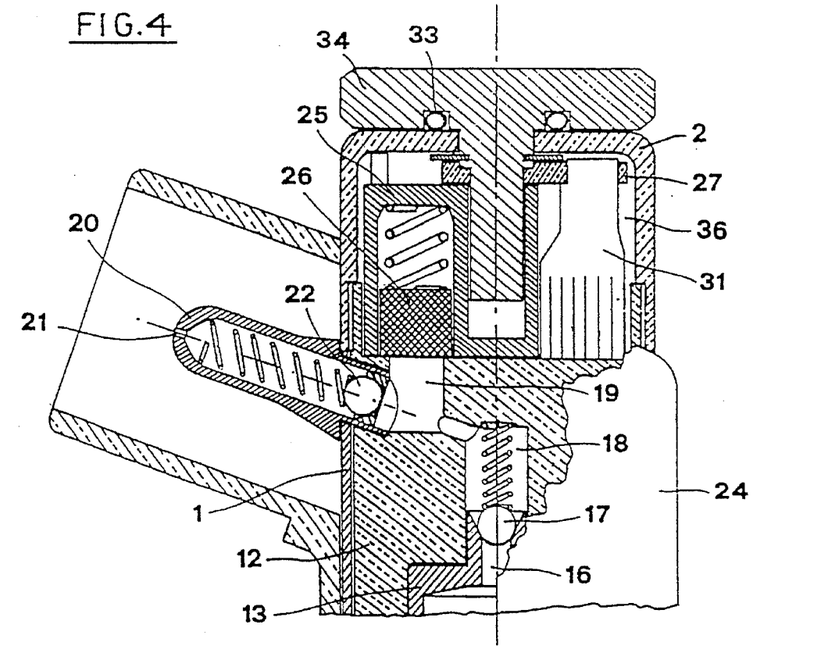
FIG. 4.—Is an axial sectional view of a detail of the dispenser showing the drug reservoir, containing the filling and separation device, and the dosage chamber.
Figures 5, 6:
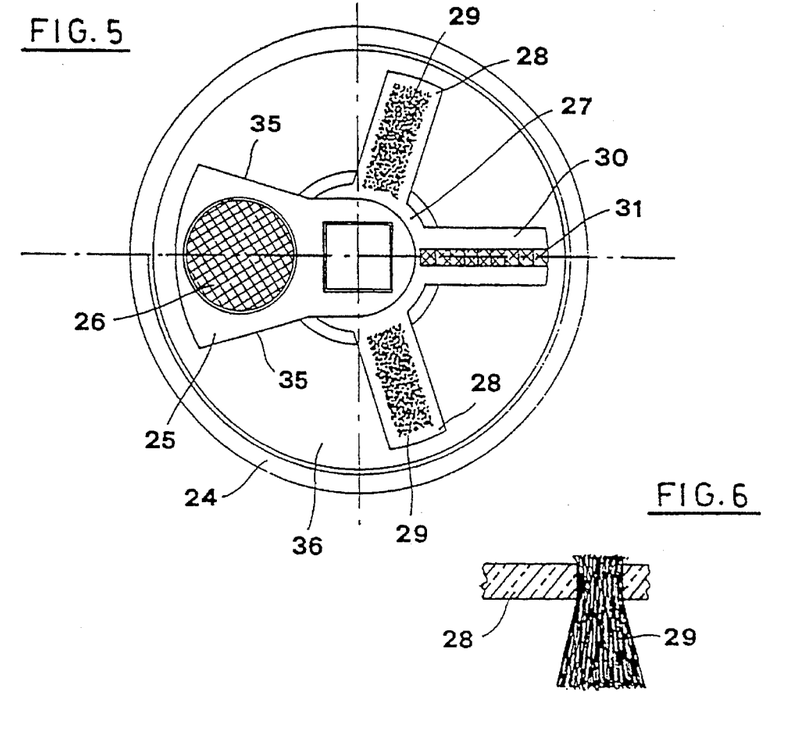
FIG. 5.—Is a plan detail view of the filling and separation element.
FIG. 6.—Is a side detail view of one of the filling brooms.

FIGS. 4, 5 and 6 show in a more detailed way the filling and separation device contained in the drug reservoir chamber 36 placed under the cover 2.

This device consists of a turning element 25, provided with vertical face 35, perpendicular to the bottom of the drug reservoir, carrying a spring loaded plug 26 made of resilient material, like rubber, and of a further turning element 27 provided with three arms, two of which 28, each carrying a filling brush or broom 29, and a central one, 30, carrying a preferably softer and longer broom 31 suitable to deeply introduce the powder inside the dosage chamber 19.

The cover 2 is axially holed and retains after assembling a seal ring 33, an actuation knob 34 provided with a square section stem holding the elements 25 and 27 which can therefore be turned by the outside.

The uniform and reproducible filling of the calibrated dosage chamber 19, is performed by vertically holding the dispenser with the drug reservoir on the top and by turning clock or anticlockwise for 380° the knob 34 and consequently the elements 25 and 27.

During this rotation the component elements perform the following functions: the broom 31, mounted on the arm 30 of the element 27, moves the micronized powder towards and into the dosage chamber 19 by entering into it and allowing the filling of its deeper portion, the brushes or brooms 29, mounted on the arms 28 of the element 27, move the powder towards the dosage chamber 19 and fill its upper portion, the perpendicular sides 35 of the element 25 remove the excess of powder and finally, once the turn is completed, the plunger 26 closes, thanks to the spring loading, the dosage chamber 19, preventing therefore the air compressed by the device previously described or the drug contained in the dosage chamber to enter or return into the drug reservoir chamber 36.

The separation granted by the plunger 26 also ensures that the powderized drug contained in the drug reservoir, never get in contact with outside air, even with the one first sucked and then ejected by the compression device.

Finally it must be noted that the small brushes or brooms are not in any way spring loaded to press against the chamber to be filled or against the powderized drug and that they simply move the micronized drug towards and into the dosage chamber, having the further task of moving and shaking the powder and to clean the edges of the dosage hole, thus removing eventual powder agglomerates or lumps which could obstacle a correct filling.

According to the invention the system, can be actuated by means of a control provided by the user's inhalation instead of by the previously described manual control obtained by continuing the actuation stroke of the plunger 3 after the first phase of loading the main spring 7.

Some modifications developed for this instance are shown in FIGS. 7 to 11 and these modifications still based on the same operating principle, will be described here below.

Figure 7:
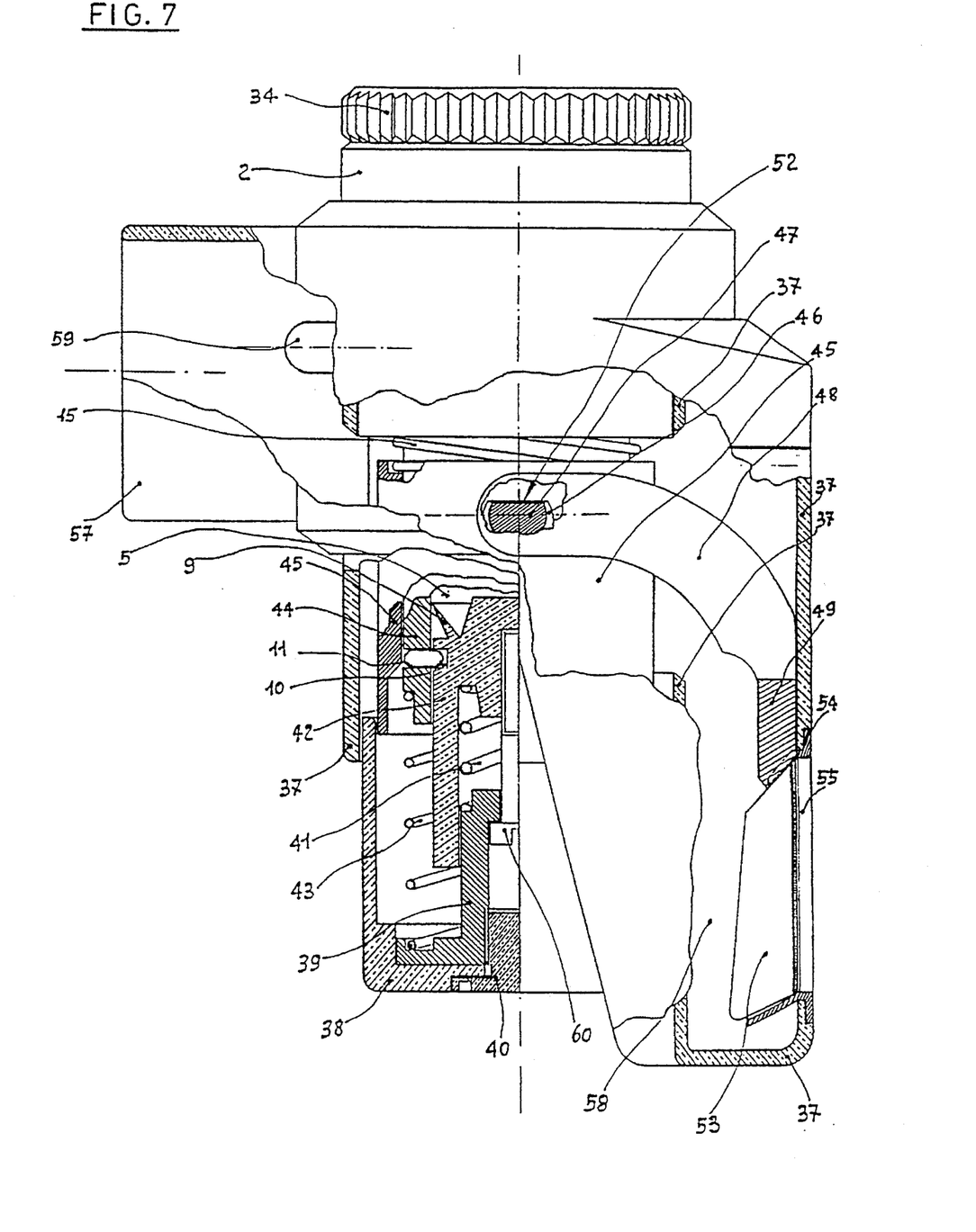
FIG. 7.—Is an axial partly sectional view of a modified embodiment of the dispenser showing the application of the breath control actuation, at the rest condition similar to the one described in FIG. 1.

FIG. 7 shows in a schematic way the inhalation actuated dispenser wherein the modified control sleeve 45, is provided with two diametrically opposite special slots 46 which house the cams 47, formed on the side arms 48 of the lever control element 49, and allow the fulcrum pins 50, of said control lever 49, to pass through and enter the blind holes 51 made on the tubular element 44 which forms the compression chamber 5 and retains, in a special slotted groove, the same resilient expansible detent ring 11 of the basic embodiment.

Figure 11:
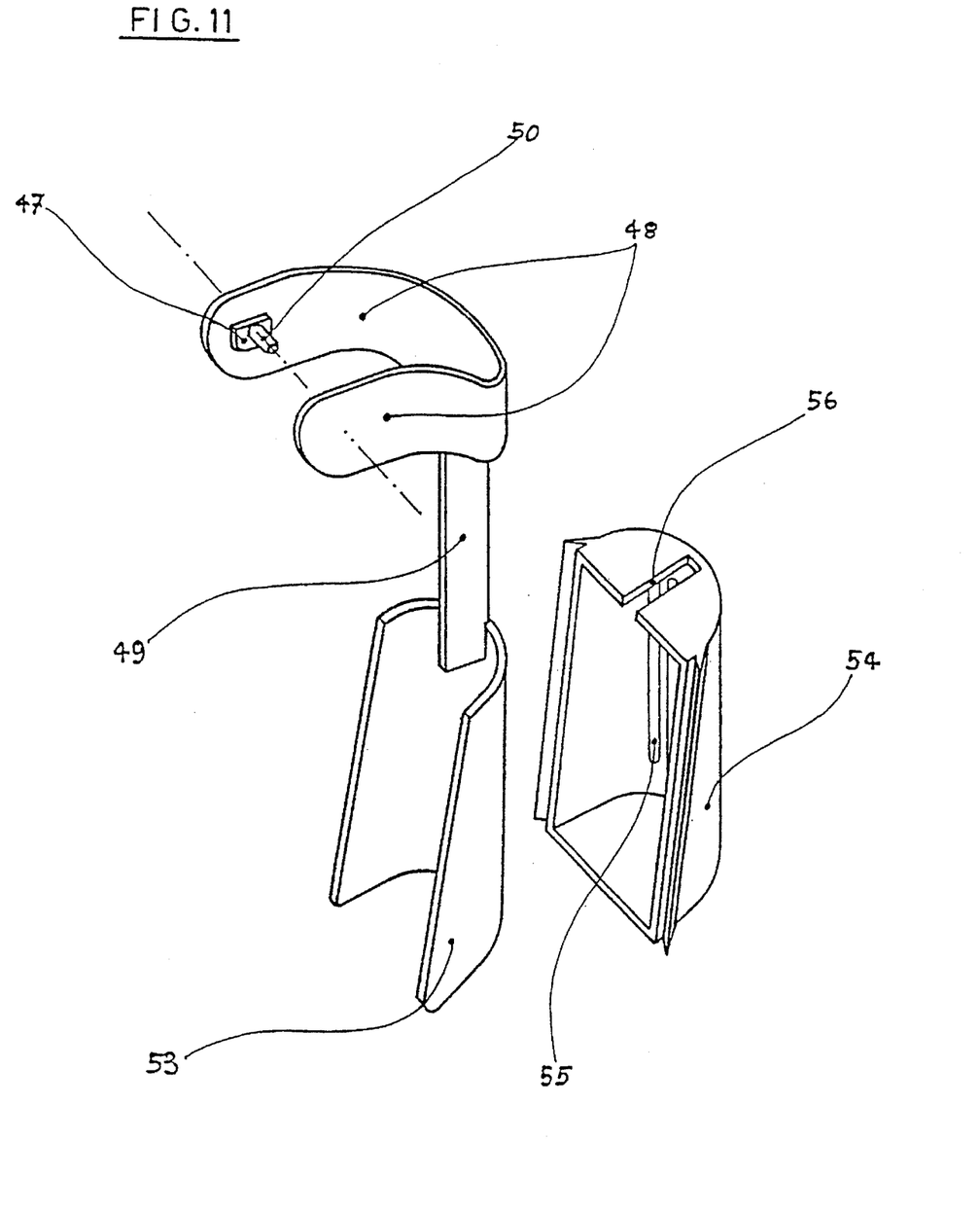
FIG. 11.—Is a perspective of the lever, complete with side arms and vane, and of the inhaled air flow conveyer element.

Said control lever 49, as better described in FIG. 11 consists of the two side arms 48 carrying the cams 47 and the fulcrum pins 50, of a centre lever arm and of an element, which is sensible to the depression caused by the inhalation, formed as a semicylindrical vane 53.

The semicylindrical vane 53 is housed into an air flow conveyer element 54, provided with slits 55, for the air inlet, and with a slit 56 to slidably house the centre arm of the control lever 49, and which is inserted and fixed into a side into an opening of the chamber 58 formed into a side portion of the main body 37; the whole such arranged that, at rest condition, the air inlet slits 55 are normally closed by the semicylindrical vane 53.

Furthermore, on respect to the basic embodiment, the control shoulder 4 has been eliminated from the actuation plunger 3 as no longer necessary, because in the breath actuated version the plunger, now 38, has the only function to compress and load the main spring 41.

Finally the dispenser described it, FIGS. 7 to 10 is provided with another secondary spring 43 which resets the plunger start position at the end of the delivery, as described later on.

The upper portion of the dispenser, not described in details in FIGS. 7 to 10, consists of the same drug reservoir, the same filling system and the same dosage chamber, which is placed in a passage between the air compression chamber 5 and the nozzle 59, of the basic embodiment.

After the dosage chamber filling, performed as previously described, the patient takes the mouthpiece 57 at his mouth and, while holding the dispenser, presses the cylindrical plunger 36 until it stops.

This action exerted on the plunger 36 causes the loading of the main spring 41, with the consequent energy accumulation within the same, as the piston 42 cannot move forward, as retained by the resilient expansible detent ring 11 which is partially inserted into the circular groove 10 of the piston 42 and the expansion the same detent ring 11 is prevented by the control sleeve 45.

At this point and while keeping pressed the cylindrical plunger 38, the patient makes an inhalation act which causes, through the mouthpiece 87 and the special passages made in the main body 37, a depression in the control chamber 58.

This depression causes the movement of the semicylindrical vane 53, and of the lever 49, which is necessary to let the air in through the slits 55 made on the air flow conveyer 54.

The result is 8 rotation of the lever 49, on its fulcrum pins 50, and of the corresponding cams 47 which, acting against the face 52 of the slots 46 made on the control sleeve 45, cause the upward movement of the latter as shown in FIGS. 2 and 4.

This upward movement of the control sleeve 45 releases the resilient expansible detent ring 11, which expands, then stopping its detent action on the piston 42 which snaps forward, instantly releasing all the energy previously accumulated by loading the main spring 41 and causing a jet of compressed air at predetermined and reproducible speed and pressure which carries, as described for the basic embodiment, the powder contained in the dosage chamber, through the nozzle, to the mouth and the lungs of the patient.

The perfect synchronization between the drug delivery and the user's inhalation, is granted, further than by the instantaneous action of the dispenser and by the fact that anybody, once started an inhalation act, tends to fully complete it, by the fact that the depth and the shape of the air flow conveyer 54 are such to allow an effective air passage, between it and the semicylindrical vane 53 edges, only when the control device has been actuated and the drug delivery occurred.

Figure 9:
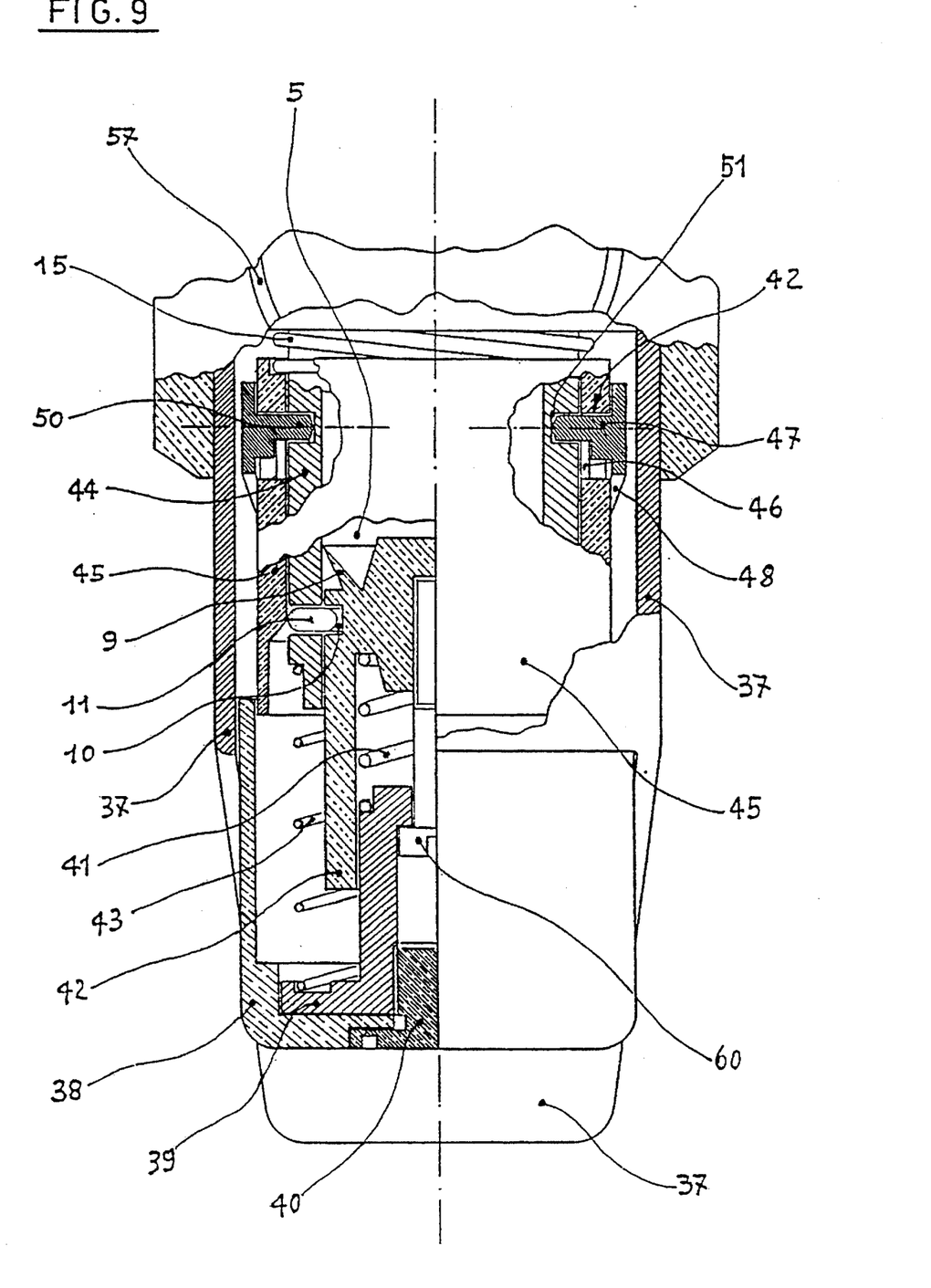
FIG. 9.—Is an axial partly sectional view of the dispenser in the same rest position of FIG. 7 but axially rotated of 90°.
Figure 10:
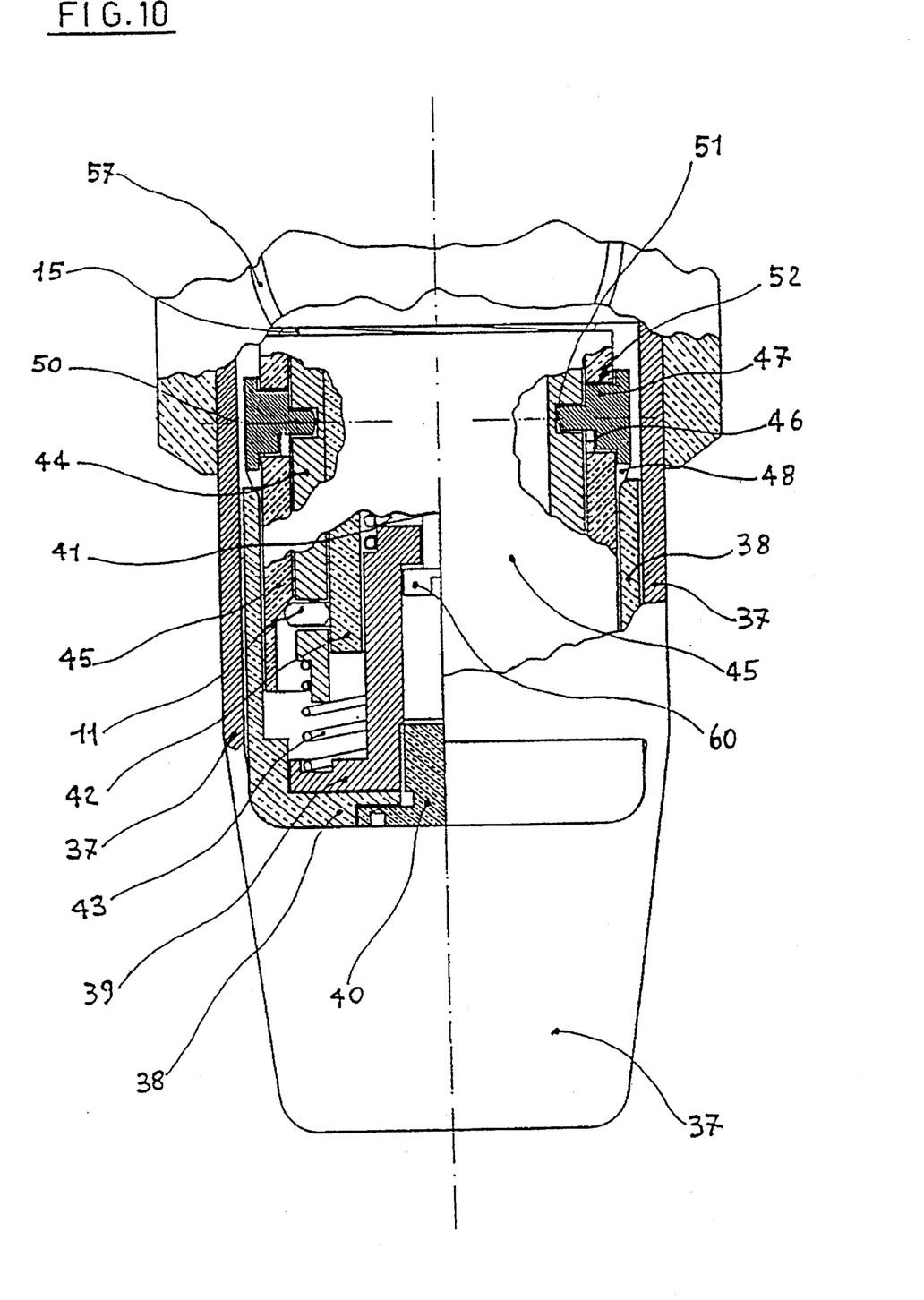
FIG. 10.—Is an axial partly sectional view of the dispenser in the same dispensing position of FIG. 8 but axially rotated of 90°.

Once the delivery has been performed and the cylindrical plunger 38 released, the return secondary spring 43 returns the unit cylindrical plunger 38/piston 42 to the rest or start position while the return secondary spring 15 provides for the return to the rest or start position of the control sleeve 45 and of the lever 49, and therefore of the resilient expansible detent ring 11, as shown in FIG. 7 and FIG. 9.

As to the remainder, all as described and shown, made of any suitable material, liable to modifications and improvements, still within the basic principle of the invention.

What is claimed is:

1. A powder jet dispenser serving as a medicament pack container for medicament inhalation therapies, comprising:

a main body portion(1);

a nozzle (20);

a drug reservoir (36) having a bottom side;

a dosage chamber (19) arranged at the bottom side of said drug reservoir (36); and a dose metering system, comprising:
   filling means for filling said dosage chamber (19), said filling means comprising:
   a separation unit (25, 26) for providing, after the filling of said dosage chamber, an air-tight separation of said filling means from said drug reservoir (36);

an air compression system comprising:
- a cylindrical compression chamber (5) formed in a tubular element (13);
- a plunger (3), the stroke of said plunger being adapted to actuate said air compression system;
- a spiral load spring (7) adapted to accumulate energy by means of its compression;
- a sliding control mechanism (11, 14) adapted to automatically release the accumulated energy of said spiral load spring (7) automatically actuated by the stroke of the plunger (3), wherein said dosage chamber (19) is connected to said compression chamber (5); and
- a piston (8), wherein said accumulated energy is released against said piston (8) which is adapted, under the thrust of said load spring (7), to snap forwardly into said compression chamber (5) thereby producing a jet of compressed air delivering the drug from the dosage chamber (19) through said nozzle (20), wherein said filling means is rotatable and said dosage chamber (19) is fixed with respect to said main body portion (1).

2. The powder jet dispenser according to claim 1, wherein said main body portion (1) has upper and lower ends, bearing on its upper end a fixed, screwed cover (2) which closes said drug reservoir (36) and disposed at the lower end said plunger (3) which is axially slidable, hollow, cylindrical and manually actuatable and which is provided with two bores forming a shoulder (4) and a plane bottom bearing a cylindrical base (6) having a seat for supporting and arresting a spiral load main spring (7) assembled in a special blind bore in the piston (8) which is axially slidable in the tubular element (13) forming said cylindrical compression chamber (5) fixed and retained by a distribution and separation head (12), said distribution and separation head (12) being provided with a downwardly protruding neck bearing a secondary return spring (15) resting against a seat formed in a control sleeve (14) which is axially slidable over the tubular element (13), said distribution and separation head (12) being fixed to the upper end of the main tubular body (1) under the drug reservoir chamber (36) which is provided with an air passage chamber (18) containing a sphere check valve (17) in correspondence with a center outlet hole (16) provided at an end of the tubular element (13) in which the piston (8) slides, said air passage chamber (18) being connected by a passage to the stationary dosage chamber (19) having an upper opening connected to the drug reservoir chamber (36) through which it can be filled, and an outlet passage connected to the nozzle (20).

3. A powder jet dispenser according to claim 1, wherein the nozzle (20) is provided with a non-return sphere check valve (22) for forming an air-tight seal.

4. A powder jet dispenser according to claim 1, wherein a head of the piston (8) is provided with a circular seal lip (9).

5. The powder jet dispenser according to claim 1, wherein said tubular element (13) has a slotted groove formed therein, said sliding control mechanism comprises:
- a resilient expansible detent ring (11) which is retained in the slotted groove of the tubular element (13);
- a circular groove (10) formed on the head of the piston (8); and
- a control sleeve (14) having a bore which comprises a cam profile adapted to force said resilient expansible detent ring to protrude inwardly towards the head of the piston (8) and to enter said circular groove (10), said control sleeve being axially slidable over the tubular element (13) to prevent a forward movement of the piston (8) during a loading stroke of the load spring (7) until the control sleeve (14) shifts upwardly releasing the resilient expansible detent ring (11) and allowing the piston (8) to snap forwardly under the thrust of the load spring (7).

6. The powder jet dispenser according to claim 5, wherein said main body portion (1) has upper and lower ends, bearing on its upper end a fixed, screwed cover (2) which closes said drug reservoir (36) and disposed at the lower end said plunger (3) which is axially slidable, hollow, cylindrical and manually actualable and which is provided with two bores forming a shoulder (4) and a plane bottom bearing a cylindrical base (6) having a seat for supporting and arresting a spiral load main spring (7) assembled in a special blind bore in the piston (8) which is axially slidable in the tubular element (13) forming said cylindrical compression chamber (5) fixed and retained by a distribution and separation head (12), said distribution and separation head (12) being provided with a downwardly protruding neck bearing a secondary return spring (15) resting against a seat formed in the control sleeve (14) which is axially slidable over the tubular element (13), said distribution and separation head (12) being fixed to the upper end of the main body portion (1) under the drug reservoir chamber (36) which is provided with an air passage chamber (18) containing a sphere check valve (17) in correspondence with a center outlet hole (16) provided at an end of the tubular element (13) in which the piston (8) slides, said air passage chamber (18) being connected by a passage to the stationary dosage chamber (19) having an upper opening connected to the drug reservoir chamber (36) through which it can be filled, and an outlet passage connected to the nozzle (20).

7. A powder jet dispenser according to claim 1, wherein the dose metering system further comprises:
- a turning knob (34) provided with a stem disposed in the drug reservoir, the stem having a square-shaped end;
- a cover (2) having a hole and bearing, the turning knob positioned in a sealed manner through a hole; and
- a second turning element (27) provided with three arms, wherein two (28) of said three arms each carry a filling brush or broom (29), and the third (30) remaining arm located centrally between said two filling brush or broom carrying arms, carries a softer and longer broom (31), suitable to deeply introduce the powder deeply into the dosage chamber (19) which is formed as a hole in the bottom of the drug reservoir chamber (36) and wherein said separation unit comprises:
- an element (25) disposed on the square-shaped end of said turning knob (34), said element (25) provided with vertical faces (35) perpendicular to the bottom side of the drug reservoir;
- separation means carried by said element (25) for separating in a sealed manner said dosage chamber (19) from said drug reservoir (36).

8. A powder jet dispenser according to claim 7, wherein the turning knob (34) rotates over a range of 360°.

9. A powder jet dispenser according to claim 7, wherein said means for separating, upon rotating said turning knob (34) to fill said dosage chamber (19), separates in a sealed manner said dosage chamber (19) from said drug reservoir (36) upon completion of the filling rotation, thereby preventing any compressed air dispersion or drug to return into the drug reservoir (36) during delivery of the drug.

10. A powder jet dispenser serving as medicament pack container for medicament inhalation therapies comprising:
- a main body portion (37);
- a nozzle (59);
- a drug reservoir (36);
- a dosage chamber (19) arranged at the bottom of said drug reservoir (36); and
- a dose metering system comprising:
  - filling means adapted to fill said dosage chamber (19), said filling means comprising:
    - a separation unit (25, 26) adapted to provide, after the filling of said dosage chamber, an air-tight separation from the drug reservoir (36), said dispenser further comprising:
- an air compression system comprising:
  - a compression cylindrical chamber (5) formed in a tubular element (44);
  - a plunger (38), the stroke of said plunger being adapted to actuate said air compression system;
  - a spiral load spring (41) adapted to accumulate energy by means of its compression;
  - a lever control element (49);
  - a sliding control mechanism (11, 45) adapted to automatically release said accumulated energy of said spiral load spring (41), said sliding control mechanism (11, 45) being automatically actuated by said lever control element (49) directly controlled by a user's inhalation, said dosage chamber (19) being connected to said compression chamber (5); and
  - a piston (42), said accumulated energy being released against said piston (42) which is adapted, under the thrust of said load spring (41), to snap forwardly into said compression chamber (5), thereby producing a jet of compressed air for delivering a drug from the dosage chamber (19) through said nozzle (20, 59), wherein said filling means is rotatable and said dosage chamber (19) is fixed with respect to said main body portion (37).

11. A powder jet dispenser according to claim 10, wherein the head of the piston (42) is provided with a circular seal lip (9).

12. A powder jet dispenser according to claim 10, wherein said sliding control mechanism comprises:
- a resilient expansible detent ring (11) retained in a slotted groove of the tubular element (44);
- a groove (10) formed on a head of the piston (42); and
- a control sleeve (45) having a bore which comprises a cam profile, said cam profile being adapted to force said resilient expansible detent ring to protrude inwardly towards the head of the piston (42) and to enter said groove (10), said control sleeve being axially slidable over the tubular element (44), thus preventing a forward movement of the piston (42) during the loading stroke of the load spring (41) of the plunger (38) until the control sleeve (45) shifts upwardly releasing the resilient expansible detent ring (11) and allowing the piston (42) to snap forwardly under the thrust of the load spring (41).

13. A powder jet dispenser according to claim 12, wherein one end of the lever control element (49) is associated with a control sleeve (45) through two arms (48), wherein the two arms (48) carry two fulcrum pins (50) which pass through two diametrically opposite slots (46) formed in the control sleeve (45) and enter two blind holes (51) formed in a modified tubular element (44); each of the fulcrum pins (50) is connected to a cam (47) housed in the slots (46) of the control sleeve (45) and interacts with upper faces (52) of the slots (46); and another end of the lever control element (49) is formed opposite to the two arms (48) as a semicylindrical vane (53) and placed in a special control chamber (58) formed in said main body portion (37) and is connected by means of suitable passages with a mouthpiece (57) of the dispenser.

14. A powder jet dispenser according to claim 13, wherein the special control chamber (58) which contains the semicylindrical vane (53) of the lever control element (49), is provided with an opening into which is inserted and fixed an air flow conveyer (54) provided with slits (55) for allowing air to enter and with a slit (56) to slidably receive the level control element (49) housing the semicylindrical vane (53); wherein inhalation by a user creates through the mouthpiece (57) and the special passages in the main body (37) a subatmospheric pressure in the control chamber (58) which causes movement of the semicylindrical vane (53) from its rest position in which it normally closes the slits (55), to a position in which said air can enter, and causing the lever control element (49) to rotate on the fulcrum pins (50) and the associated cams (47), which by interacting with the upper faces (52) of the slots (46) formed on the control sleeve (45) forces the control sleeve (45) to shift allowing the resilient expansible detent ring (11) to expand, thus releasing the piston (42) which snap forwardly, under thrust of the load spring (41) previously loaded by a compression stroke of the plunger (38), producing a jet of compressed air at a predetermined pressure and speed.

15. A powder jet dispenser according to claim 14, wherein the inner surface of the air flow conveyer (54) matches the outer surface of the semicylindrical vane (53) and said conveyer (54) has a depth which is higher than the depth of said vane (53) at such an extent to force the control lever (49) to rotate long enough for delivery of the drug to occur, before air is allowed to enter the control chamber (58).

16. A powder jet dispenser according to claim 10, wherein one end of the lever control element (49) is associated with a control sleeve (45) through two arms (48), wherein the two arms (48) carry two fulcrum pins (50) which pass through two diametrically opposite slots (46) formed in the control sleeve (45) and enter two blind holes (51) formed in a modified tubular element (44); each of the fulcrum pins (50) is connected to a cam (47) housed in the slots (46) of the control sleeve (45) and interacts with upper faces (52) of the slots (46); and another end of the lever control element (49) is formed opposite to the two arms (48) as a semicylindrical vane (53) and placed in a special control chamber (58) formed in said main body portion (37) and is connected by means of suitable passages with a mouthpiece (57) of the dispenser.

17. A powder jet dispenser according to claim 16, wherein the special control chamber (58) which contains the semicylindrical vane (53) of the control lever (49), is provided with an opening into which is inserted and fixed an air flow conveyer (54) provided with slits (55) for allowing air to enter and with a slit (56) to slidably receive the control lever (49) housing the semicylindrical vane (53); wherein inhalation by a user creates through the mouthpiece (57) and the special passages in the main body portion (37) a subatmospheric pressure in the control chamber (58) which causes movement of the semicylindrical vane (53) from its rest position in which it normally closes the slits (55), to a position in which said air can enter, and causing the control lever (49) to rotate on the fulcrum pins (50) and the associated cams (47), which by interacting with the upper faces (52) of the slots (46) formed on the control sleeve (45)

forces the control sleeve (45) to shift allowing the resilient expansible detent ring (11) to expand, thus releasing the piston (42) which snap forwardly, under thrust of the load spring (41) previously loaded by a compression stroke of the plunger (38), producing a jet of compressed air at a predetermined pressure and speed.

18. A powder jet dispenser according to claim 17, wherein the inner surface of the air flow conveyer element (54) matches the outer surface of the semicylindrical vane (53) and said conveyer (54) has a depth which is higher than the depth of said vane (53) at such an extent to force the control lever (49) to rotate long enough for delivery of the drug to occur, before air is allowed to enter the control chamber (58).

19. A powder jet dispenser according to claim 10, wherein the dose metering system further comprises:

a turning knob (34) provided with a stem disposed in the drug reservoir, the stem having a square-shaped end;

a cover (2) having a hole and bearing the turning knob positioned in a sealed manner through a hole; and a second turning element (27) provided with three arms, wherein two (28) of said three arms each carry a filling brush or broom (29), and the third (30) remaining arm located centrally between said two filling brush or broom carrying arms, carries a preferably softer and longer broom (31), suitable to introduce the powder deeply into the dosage chamber (19) which is formed as a hole in the bottom of the drug reservoir chamber (36), and wherein said separation unit comprises:

an element (25) disposed on the square-shaped end of said turning knob (34), said element (25) provided with vertical faces (35) perpendicular to the bottom side of the drug reservoir (36);

separation means carried by said element (25) for separating in a sealed manner said dosage chamber (19) from said drug reservoir (36).

20. A powder jet dispenser according to claim 19, wherein the turning knob (34) rotates over a range of 360°.

21. A powder jet dispenser according to claim 19, wherein said means for separating, upon rotating said turning knob (34) to fill said dosage chamber (19), separates in a sealed manner said dosage chamber (19) from said drug reservoir (36), upon completion of the filling rotation, preventing any compressed air dispersion or drug to return into the drug reservoir (36) during delivery of the drug.

* * * * *